United States Patent [19]

Papa

[11] 4,434,301
[45] Feb. 28, 1984

[54] PRODUCTION OF LOW COLOR REFINED ISOPHORONE

[75] Inventor: Anthony J. Papa, St. Albans, W. Va.

[73] Assignee: Union Carbide Corporation, Danbury, Conn.

[21] Appl. No.: 411,280

[22] Filed: Aug. 25, 1982

[51] Int. Cl.³ .......................... C07C 45/85; B01D 3/38
[52] U.S. Cl. ..................... 568/366; 203/36; 203/37; 203/35
[58] Field of Search .................... 568/366; 203/36, 37, 203/35

[56] References Cited

U.S. PATENT DOCUMENTS

| | | | |
|---|---|---|---|
| 2,351,352 | 6/1944 | McAllister et al. | 568/366 |
| 2,429,484 | 10/1944 | Peters | 568/366 |
| 3,276,973 | 10/1976 | Burmaster et al. | 568/366 |
| 3,337,423 | 8/1967 | Schmitt et al. | 568/366 |
| 3,337,632 | 0/0000 | Schmitt et al. | 568/366 |
| 3,337,633 | 8/1967 | Schmitt et al. | 568/366 |
| 3,397,120 | 8/1968 | Deana et al. | 568/366 |
| 3,462,348 | 8/1969 | Wellman et al. | 568/366 |
| 3,770,829 | 11/1973 | Wellman et al. | 568/366 |
| 3,981,918 | 9/1976 | Walton et al. | 568/366 |
| 4,248,673 | 2/1981 | Cheminal et al. | 203/37 |

FOREIGN PATENT DOCUMENTS 1000574  8/1965  United Kingdom ............... 568/366

*Primary Examiner*—James H. Reamer
*Attorney, Agent, or Firm*—Bernard Francis Crowe

[57] ABSTRACT

Crude isophorone is refined by contacting it with aqueous caustic followed by washing and fractional distillation.

9 Claims, No Drawings

PRODUCTION OF LOW COLOR REFINED ISOPHORONE

BACKGROUND OF THE INVENTION

This invention pertains to the refining of isophorone and particularly to a process for reducing the color in crude isophorone.

Isophorone is used in industrial solvents and as a chemical intermediate for the synthesis of resins, dyes, insecticides, and like. It is generally made by the ALDOL condensation of acetone which results in contamination of the main product with many by-products, such as, 4,6-dimethylhepta-3,5-diene-2-one, 3,5,5-trimethylcyclohex-3-ene-1-one, phorone, mesitylene, 2,2,6,6-tetramethyl tetrahydropyran-4-one, xylitones and isoxylitones, 3,3,6,8-tetramethyl-1-tetralone, and the like.

There is a need for an efficient method of treating crude isophorone to produce a low colored, refined product.

BACKGROUND ART

Current industrial approaches to this color problem employ acidic reagents which have severe limitations, e.g., they require neutralization, cause high acidity in the final product, are expensive and/or cause loss of isophorone by reaction during treatment. More specifically, acidic ion-exchange resins and fuller's earth are used commercially but are unsatisfactory because of the high costs and the requirement for special process equipment. For example, columns to contain the reagents, man power for maintaining the containing columns, regeneration of the reagents and the loss of significant amounts of isophorone during the treatment detract from the usefulness of the prior art methods of purification of isophorone.

Some of the methods from the patent literature which have been used for this problem include the following:

1. U.S. Pat. No. 4,248,673 teaches the decolorization of crude isophorone with acid exchange resins followed by neutralization with excess alkaline reagent, washing with sufficient water to dissolve the salts formed and distilling the organic layer under reduced pressure to obtain low color refined isophorone. Undesireable features of this process include: high cost of the ion exchange resin, necessity of regeneration of the ion exchange resin, need for a holding tank for the acid used for regenerations, the disposal of the effluent after regeneration and corrosion.

2. U.S. Pat. No. 4,059,632 discloses the decolorization of crude of isophorone by treatment with either phosphoric acid or para-toluenesulfonic acid for at least seven hours at 130°-190° C. The long residence times required and corrosion are problems with this approach.

3. British Pat. No. 832,124 teaches the decolorization of crude isophorone by contacting the isophorone by an acid washed fuller's earth at an elevated temperature and recovering refined isophorone by distillation. A major drawback in this method is the variability of the fuller's earth. This reagent degenerates quickly first by showing acid drool and then quickly losing its effectiveness, requiring frequent change to a fresh batch of reagent.

4. British Pat. No. 833,099 discloses a process of decolorizing isophorone by mixing crude isophorone with an aromatic sulfonic acid, such as, p-toluene sulfonic acid and distilling refined, low color isophorone from the mixture. The neutralization required followed by water washings and corrosion of the equipment are drawbacks to this solution of the problem.

It is an object of this invention to provide a method for decolorizing crude isophorone.

Other objects will become apparent to those skilled in the art upon a reading of the specification.

DISCLOSURE OF THE INVENTION

A method of decolorizing crude isophorone made by the vapor phase reaction of acetone over a heterogeneous aldol condensation catalyst has been found which comprises contacting crude isophorone with a strong caustic aqueous solution at a temperature of about 140° C. to about 200° C., washing the treated isophorone with water until a pH of about 7 is obtained and then recovering decolorized isophorone by fractional distillation.

The choice of strong caustic reagent is not narrowly critical and so while sodium hydroxide is preferred for economic reasons any strong alkali metal or alkaline earth hydroxide or oxide can be used in a liquid-phase homogenous or heterogeneous process. For example, potassium hydroxide, lithium hydroxide, calcium oxide, magnesium hydroxide, and the like can be used.

The preferred limits of sodium hydroxide for use in this invention are about 0.1 to about 0.8 weight percent used as an aqueous 20 percent by weight solution. The use of levels higher than 0.8 weight percent sodium hydroxide tend to produce stable emulsions after treatment of the crude isophorone which interferes with the separation of the aqueous and oil phases.

The process of this invention in general involves heating impure isophorone containing color formers and color bodies for about one to two hours at the maximum allowable temperature along with an aqueous solution of the caustic reagent.

After heating the treated mixture, caustic was removed by washing with water until the washings showed a pH of 7 as indicated by pH indicator paper. It is essential that the treated material be freed of alkalinity to avoid excessive isophorone losses during subsequent distillation.

The wet organic phase is then batch distilled and 6 fractions collected. Fractions III to VI contain refined, low color isophorone. Typical distillation results of untreated crude isophorone and sodium hydroxide treated material have been compared.

The invention is further described in the examples which follow. All parts and percentages are by weight unless otherwise specified.

EXPERIMENTAL EXAMPLES

Distillation

Distillations were conducted with 300 gram charges in a batch mode and attempts were made to consistently obtain six fractions with the following percent of feed.

|  | Percent Feed |
| --- | --- |
| Cut I | 10 |
| Cut II | 15 |
| Cut III | 10 |
| Cut IV | 35 |
| Cut V | 5 |
| Cut VI | 5 |

| -continued | |
|---|---|
| | Percent Feed |
| Residue | 20 |

Cuts I and II contain lights color bodies, mesitylene and most of the phorone and 3,5,5-trimethyl-3-cyclohexene-1-one. Cuts III to VI are considered refined isophorone.

Methods of Analysis

Color

Most of the color determinations were made by comparing colors of samples contained in tall-form Nessler tubes against a series of platinum-cobalt standards of equal volume in identical tubes. The Gardner color system was used for the remainder.

pressure. During this time refluxing of a lights commenced and a darkening of the reaction mixture occurred (from Gardner 13 to 18). Darkening is characteristic of transformations occurring of color formers into high boiling color bodies. After cooling to room temperature the mixture was washed with 5 100-ml. portions of water or until the washings were neutral to pH indicator paper.

300 Grams of the above treated mixture was charged into a 1-liter kettle of a 20-tray, 1-inch diameter, vacuum jacketed and silvered Oldershaw distillation column. Distillation at a rate of reflux of 2:1 (in/out) gave six fractions (plus residues) under the conditions shown below and the color of each determined as shown in Table I. The composition of the untreated crude isophorone is presented in the first column under the caption "Untreated" for comparison.

TABLE I

DISTILLATION OF CRUDE ISOPHORONE TREATED WITH 0.6 w/w OF SODIUM HYDROXIDE

| | | Composition | | | | | | | |
|---|---|---|---|---|---|---|---|---|---|
| | | NaOH 0.6 wt % | Distillation of NaOH Treated Sample[d] | | | | | | |
| Component[a] | Untreated | 130° C./1 hr | I | II | III | IV | V | VI | Residue[b] |
| Acetone | 0 | 0.10 | 0 | 0 | 0 | 0 | 0 | 0 | 0 |
| Water | 0.18 | 6.23 | 5.54 | 0.57 | 0.53 | 0.36 | 0.33 | 0.27 | 0.25 |
| Mesityl Oxide | 0 | 0.42 | 0.10 | 0 | 0 | 0 | 0 | 0 | 0 |
| Mesitylene | 0.03 | 0.02 | 0.15 | 0 | 0 | 0 | 0 | 0 | 0 |
| Unknown lights | 0.04 | 0 | 0 | 0 | 0 | 0 | 0 | 0 | 0 |
| 3,5,5-Trimethyl-3-cyclohexene-1-one | 0.27 | 1.08 | 5.72 | 1.26 | 0.92 | 0.64 | 0.24 | 0.13 | 0 |
| Phorone | 1.92 | 1.30 | 9.38 | 1.86 | 0.64 | 0.20 | 0.02 | 0 | 0 |
| Isophorone | 93.40 | 85.33 | 78.05 | 95.84 | 97.92 | 98.80 | 99.24 | 99.43 | 26.52 |
| Unknown heavies | 1.72 | 3.18 | 1.06 | 0.45 | 0 | 0 | 0.18 | 0.17 | 12.23 |
| 3,3,6,8-Tetramethyl-1-tetralone | 2.48 | 2.34 | 0 | 0 | 0 | 0 | 0 | 0 | 9.08 |
| Non-Volatile residues | | | | | | | | | 51.92 |
| Weight, gms | | 300.[c][g] | 30.8[e] | 40.3 | 30.2 | 98.1 | 16.6 | 14.0 | 54.4 |
| Colors, Pt-Co[f] | 13 G | 18 G | 3 G | 19 | 40 | 15 | 15 | 15 | 18 G |

[a]Analysis by gas chromatography in area %
[b]Residue analysed by gas chromotography using an internal standard (acetone) in wt. %
[c]Amount of material distilled
[d]Cold traps contained 9.6 grams
[e]Includes 7.0 g of a water layer
[f]G = Gardner color scale used. Others were measured by Pt-Co standards.
[g]Isophorone Accountability = 89.27% out/in.

Purity/Compositions

Samples were analyzed using a Bendix 2200 instrument with a thermal conductivity detector. Compositional analyses are given in area percent with the exception of kettle samples in which case weight percent is reported (obtained by using acetone as an internal standard).

Column: Stainless steel (10 feet × ⅛ inch) packed with 20% Carbowax 20M on Chromosorb T 40/60 mesh.
Conditions: Programmed from 70° to 220° C. at 4° C./min.
Injector Port Temperature: 235° C.
Detector Temperature: 250° C.
Helium Flow: 30 ml/min.
Sample Size: 2 ul (microliters)

EXAMPLE 1

400 grams of crude isophorone having a dark color and several impurities determined by analysis as shown in Table I was placed into a 1-liter glass reactor together with 12.0 grams of a 20 wt. % aqueous solution of sodium hydroxide (this corresponds to 0.6 wt. % sodium hydroxide based on the crude isophorone). The reaction was equipped with a thermometer, condenser, and mechanical agitator. The mixture was heated under a nitrogen atmosphere for 1 hour at 130° C. at atmospheric

| | I | II | III | IV | V | VI |
|---|---|---|---|---|---|---|
| Temperature, head, °C. | 106 | 139 | 140 | 140 | 137 | 130 |
| Temperature, 5th Tray, °C. | 138 | 137 | 137 | 137 | 135 | 130 |
| Temperature, 10th Tray, °C. | 142 | 143 | 143 | 142 | 140 | 134 |
| Temperature, kettle, °C. | 150 | 150 | 150 | 155 | 165 | 178 |
| Pressures, mm | 93 | 90 | 90 | 89 | 81 | 64 |

EXAMPLE 2-4

Example 1 was repeated using differing amounts of sodium hydroxide solution. The temperatures and exposure times employed and the results obtained are given in Table II. In order to show the efficacy of the treatment with sodium hydroxide, the composition of the untreated crude isophorone and resulting color of the various fractions after distillation (from Table III) are also shown with data from Example 1.

CONTROL A 300 grams of the same crude isophorone sample used in Examples 1-4 containing color impurities, having a dark color (Gardner 13), and the analysis as shown in Table I was placed into a 1-liter glass kettle and distilled under the same conditions as used for Examples 1–4 (reduced pressure at a 2:1 reflux ratio, through a 20-tray, 1-inch, vacuum jacketed and silvered Oldershaw column). The following fractions were collected under the conditions shown and the color of each determined (See Table III for properties).

|  | I | II | III | IV | V | VI |
|---|---|---|---|---|---|---|
| Temperature, head, °C. | 133 | 142 | 142 | 142 | 142 | 140 |
| Temperature, 5th Tray, °C. | 137 | 141 | 140 | 140 | 140 | 140 |
| Temperature, 10th Tray, °C. | 146 | 145 | 144 | 144 | 144 | 144 |
| Temperature, kettle, °C. | 151 | 150 | 150 | 153 | 161 | 174 |
| Pressures, mm | 101 | 95 | 95 | 93 | 93 | 92 |

TABLE II

ISOPHORONE DECOLORIZATION WITH SODIUM HYDROXIDE

| | | Isophorone Treated with NaOH | | | |
|---|---|---|---|---|---|
| | Isophorone Untreated | 0.1 wt. % 180° C./1 hr. Example 2 | 0.2 wt. % 155° C./1 hr. Example 3 | 0.4 wt. % 140° C./1 hr. Example 4 | 0.6 wt. % 130°/1 hr. Example 1 |
| Composition[a] | | | | | |
| Acetone | 0 | 0.02 | 0.03 | 0.12 | 0.10 |
| Water | 0.18 | 6.02 | 6.20 | 6.16 | 6.23 |
| Mesityl Oxide | 0 | 0.09 | 0.23 | 0.37 | 0.42 |
| Mesitylene | 0.03 | 0 | 0 | 0.03 | 0.02 |
| Unknown lights | 0.04 | 0 | 0 | 0 | 0 |
| 3,5,5-Trimethyl-3-cyclohexene-1-one | 0.27 | 0.98 | 1.05 | 1.03 | 1.08 |
| Phorone | 1.92 | 1.81 | 1.48 | 1.27 | 1.30 |
| Isophorone | 93.40 | 85.27 | 85.38 | 85.74 | 85.33 |
| Unknown heavies | 1.72 | 3.43 | 3.25 | 2.62 | 3.18 |
| 3,3,6,8-tetramethyl-1-tetralone | 2.48 | 2.35 | 2.38 | 2.64 | 2.34 |
| Color, gardner | 13 | 17 | 18 | 18 | 18 |
| Sodium, ppm[f] | 3.0 | ND[g] | ND[g] | ND[g] | 5.2 |
| Distillation | | | | | |
| Color, gardner Cut I[b] | 4 | 4 | 4 | 3 | 1 |
| Color, gardner Cut II[b] | 2 | 2 | 2 | 1 | 1 |
| Color, Pt-Co, Cut III[c] | 80 | 70 | 80 | 60 | 40 |
| Color, Pt-Co, Cut IV[c] | 30 | 25 | 25 | 20 | 15 |
| Color, Pt-Co, Cut V[c] | 30 | 20 | 20 | 15 | 15 |
| Color, Pt-Co, Cut VI[c] | 80 | 20 | 20 | 15 | 15 |
| Isophorone Purity %[d] | 98.9 | 99.0 | 99.8 | 98.9 | 98.9 |
| Isophorone Recovery, %[e] | 88.0 | 87.7 | 86.0 | 89.1 | 89.3 |

[a]Analysis are by gas chromatography in area %
[b]Color on the gardner scale
[c]Color on the Pt-Co Scale
[d]Purity of Cut IV which represents the center fraction
[e]Amount of isophorone accounted for in all the cuts (including residue) after distillation
[f]By atomic absorption
[g]ND = Not determined

TABLE III

DISTILLATION OF UNTREATED CRUDE ISOPHORONE

| Component [a] | Composition Untreated | Composition of Cuts After Distillation[e] | | | | | | |
|---|---|---|---|---|---|---|---|---|
| | | I | II | III | IV | V | VI | Resisue |
| Acetone | 0 | 0 | 0 | 0 | 0 | 0 | 0 | 0 |
| Water | 0.18 | 0.38 | 0.29 | 0.30 | 0.21 | 0.35 | 0.37 | 0.32 |
| Mesityl Oxide | 0 | 0 | 0 | 0 | 0 | 0 | 0 | 0 |
| Mesitylene | 0.03 | 0.17 | 0 | 0 | 0 | 0 | 0 | 0 |
| Unknown lights | 0.04 | 0.07 | 0 | 0 | 0 | 0 | 0 | 0 |
| 3,5,5,-trimethyl-3-cyclohexene-1-one | 0.27 | 13.65 | 1.31 | 0.92 | 0.63 | 0.20 | 0.53 | 0.09 |
| Phorone | 1.92 | 11.50 | 2.82 | 1.12 | 0.27 | 0.04 | 0.02 | 0.01 |
| Isophorone | 93.40 | 74.01 | 95.58 | 97.66 | 98.85 | 99.41 | 99.08 | 33.92 |
| Unknown heavies | 1.72 | 0.21 | 0 | 0 | 0 | 0 | 0 | 6.78 |
| 3,3,6,8-Tetramethyl-1-tetralone | 2.48 | 0 | 0 | 0 | 0 | 0 | 0 | 10.14 |
| Non-volitile residues | | | | | | | | 48.25 |
| Weight, gms | 300[b][e] | 31.4 | 42.8 | 31.0 | 104.4 | 16.5 | 16.1[c] | 49.2 |
| Color, Pt-Co | 13 | 4 G[d] | 2 G[d] | 80 | 30 | 30 | 80 | 18 G[d] |

[a]Analysis by gas chromatography in area % except in the case of residues when an internal standard (acetone) was employed and thus weight percent is reported
[b]Amount of material distilled
[c]Cold traps contained 3.0 grams
[d]G = Gardner color scale
[e]Isophorone Accountability = 88.04% out/in.

EXAMPLE 5 AND CONTROL B

It is extremely important to remove sodium hydroxide from crude isophorone batches treated with sodium hydroxide before distillation. If this is not done excessive losses of isophorone take place together with isomerization of isophorone to its unconjugated isomer. This renders the instant process economically impractical Thus, when an unwashed batch of crude isophorone which contained 0.05 weight percent sodium hydroxide was distilled only 64 percent of the isophorone was recovered. See Table IV for the data relative to Control B.

In contrast, when a similar batch of crude isophorone which has been water washed after caustic treatment until only 3 parts per million of sodium remained was distilled 88 weight percent of the isophorone was recovered. See Table V for data pertaining to Example 5.

The recovered isophorone in all of the Examples exhibited good color characteristics.

TABLE IV
CRUDE ISOPHORONE BATCH DISTILLATION CONTAINING NaOH
CONTROL B

| | Feed Composition gc, area-%[e] | Material Balance, grams (L) | | | | | | | | |
|---|---|---|---|---|---|---|---|---|---|---|
| Component | | Feed(g) 300 | I 29.7 | II 43.3 | III 30.8 | IV 93.5 | V 16.1 | VI 18.6 | Kettle 56.2 | Total out, grams | Recovery % Out/In |
| Acetone | 0.0 | 0.00 | 0.00 | 0.00 | 0.003 | 0.00 | 0.01 | 0.00 | | 0.013 | |
| Water | 0.18 | 0.54 | 0.12 | 0.08 | 0.05 | 0.14 | 0.05 | 0.04 | | 0.48 | |
| MSO Isomer[a] | 0.00 | 0.00 | 0.0 | 0.00 | 0.00 | 0.00 | 0.00 | 0.00 | | 0.00 | |
| MSO[a] | 0.00 | 0.00 | 0.0 | 0.00 | 0.00 | 0.00 | 0.00 | 0.00 | | 0.00 | |
| Mesitylene | 0.03 | 0.09 | 0.09 | 0.00 | 0.00 | 0.00 | 0.00 | 0.00 | | 0.09 | 100 |
| Unknown Lts.[f] | 0.00 | 0.00 | 0.76 | 0.00 | 0.00 | 0.00 | 0.00 | 0.00 | | 0.76 | |
| TMCH[b] | 2.22 | 6.66 | 16.78 | 11.80 | 5.71 | 12.73 | 1.98 | 3.02 | | 52.02 | 781 |
| Phorone | 2.61 | 7.83 | 1.46 | 0.47 | 0.18 | 0.31 | 0.02 | 0.03 | | 2.47 | 32 |
| Isophorone | 90.85 | 272.55 | 10.23 | 30.74 | 24.82 | 80.32 | 14.04 | 15.51 | | 175.66 | 64 |
| 1,4-dione[c] | 0.00 | 0.00 | 0.0 | 0.00 | 0.00 | 0.00 | 0.00 | 0.00 | | 0.00 | |
| Unknown Heavies | 1.82 | 5.46 | 0.25 | 0.22 | 0.03 | 0.00 | 0.00 | 0.00 | | 0.50 | |
| Tetralone[d] | 2.28 | 6.84 | 0.0 | 0.00 | 0.00 | 0.00 | 0.00 | 0.00 | | 0.00 | |
| | | 299.97 | 29.69 | 43.31 | 30.793 | 93.5 | 16.1 | 18.6 | 56.2 | 288.193 | |
| Sodium, % | | 0.05 | | | | | | | Cold | 2.8 | |
| | | | | | | | | | Traps | 290.993 | |
| Distribution: | | | | | | | | | | | |
| Pressure, mm | | | 102 | 101 | 99 | 99 | 99 | 97 | | | |
| Temperature, Kettle, °C. | | | 152 | 158 | 164 | 172 | 181 | 191 | | | |
| Temperature, 5th tray, °C. | | | 137 | 138 | 138 | 138 | 139 | 138 | | | |
| Temperature, 10th tray, °C. | | | 140 | 144 | 143 | 144 | 144 | 143 | | | |
| Temperature, head, °C. | | | 125 | 137 | 138 | 139 | 140 | 137 | | | |
| Color, Pt-Co | 10 G[j] | | 3 G[j] | 80 | 15 | 15 | 15 | 15 | | | |

[a]MSO = mesityl oxide
[b]3,5,5-Trimethyl-3-Cyclohexene-1-one
[c]2,2,6-Trimethyl-5-cyclohexane-1,4-dione
[d]3,3,6,8-Tetramethyl-1-tetralone
[e]By gas chromatography
[f]Light fractions
[g]Grams of crude isophorone distilled to which NaOH had been added to make the material 0.05% caustic.
[h]Grams of each cut obtained. Total grams = 291.00. The difference of 300 − 291 = 9 grams represent hold-up in the distillation columns. The kettle sample was not analyzed (accidentally destroyed). However, of ten other similar distillations isophorone content of the kettle ranged from 10–15 grams. Assuming 15 grams of isophorone was contained in this kettle sample the recovery would be 70.0%; even assuming as much as 20 gram only 71.8% isophorone recovery is obtained. Even assuming the highly unlikely case that the kettle sample is pure isophorone the recovery would only be 85.1%.
[j]G = gardner color scale. All other figures measured on Pt-Co scale.

TABLE V
DISTILLATION OF WASHED ISOPHORONE AFTER CAUSTIC TREATMENT
EXAMPLE 5

| | Feed Composition gc, area-% | Material Balance, grams (g) | | | | | | | | |
|---|---|---|---|---|---|---|---|---|---|---|
| Component | | Feed[f] 300 | I 29.7 | II 43.3 | III 30.8 | IV 93.5 | V 16.1 | VI 18.6 | Kettle 56.2 | Total out, grams | Recovery % Out/In |
| Acetone | 0.00 | 0.00 | 0.00 | 0.00 | 0.00 | 0.00 | 0.00 | 0.00 | 0.00 | 0.00 | |
| Water | 0.17 | 0.51 | 0.12 | 0.12 | 0.09 | 0.22 | 0.06 | 0.06 | 0.16 | 0.83 | |
| MSO Isomer[a] | 0.00 | 0.00 | 0.00 | 0.00 | 0.00 | 0.00 | 0.00 | 0.00 | 0.00 | 0.00 | |
| MSO[a] | 0.00 | 0.00 | 0.00 | 0.00 | 0.00 | 0.00 | 0.00 | 0.00 | 0.00 | 0.00 | |
| Mesitylene | 0.01 | 0.03 | 0.05 | 0.00 | 0.00 | 0.00 | 0.00 | 0.00 | 0.00 | 0.05 | 167 |
| Unknown Lights | 0.04 | 0.12 | 0.02 | 0.00 | 0.00 | 0.00 | 0.00 | 0.00 | 0.00 | 0.02 | |
| TMCH[b] | 0.27 | 0.81 | 4.29 | 0.56 | 0.29 | 0.66 | 0.03 | 0.09 | 0.04 | 5.96 | 736 |
| Phorone | 1.92 | 5.76 | 3.61 | 1.21 | 0.35 | 0.28 | 0.01 | 0.003 | 0.005 | 5.468 | 95 |
| Isophorone | 93.40 | 280.20 | 23.24 | 40.91 | 30.27 | 103.20 | 16.40 | 15.95 | 16.69 | 246.66 | 88[l] |
| 1,4-dione[c] | 0.01 | 0.03 | 0.00 | 0.00 | 0.00 | 0.00 | 0.00 | 0.00 | 0.24 | 0.24 | |
| Unknown Heavies | 1.72 | 5.16 | 0.07 | 0.00 | 0.00 | 0.00 | 0.00 | 0.00 | 3.34 | 3.41 | 66 |
| Tetralone[d] | 2.48 | 7.44 | 0.00 | 0.00 | 0.00 | 0.00 | 0.00 | 0.00 | 4.99 | 4.99 | 67 |
| N.V. Res.[e] | NA[h] | | | | | | | | 23.74 | 23.74 | |
| | | 300.06 | 31.4 | 42.8 | 31 | 104.36 | 16.5 | 16.103 | 49.205 | 291.368 | |
| Sodium, ppm[k] | | 3.0[j] | | | | | | | Cold | 3.0 | |
| | | | | | | | | | Traps | 294.368 | |
| Distribution: | | | | | | | | | | | |
| Pressure, mm | | | 101 | 95 | 95 | 93 | 93 | 92 | | | |
| Temperature, Kettle, °C. | | | 151 | 150 | 150 | 153 | 161 | 174 | | | |
| Temperature, 5th tray, °C. | | | 137 | 141 | 140 | 140 | 140 | 140 | | | |
| Temperature, 10th tray, °C. | | | 146 | 145 | 144 | 144 | 144 | 144 | | | |

TABLE V-continued

DISTILLATION OF WASHED ISOPHORONE AFTER CAUSTIC TREATMENT
EXAMPLE 5

| Component | Feed Composition gc, area-% | Feed[f] 300 | I 29.7 | II 43.3 | III 30.8 | IV 93.5 | V 16.1 | VI 18.6 | Kettle 56.2 | Total out, grams | Recovery % Out/In |
|---|---|---|---|---|---|---|---|---|---|---|---|
| Temperature, head, °C. | | | 133 | 142 | 142 | 142 | 142 | 140 | | | |
| Color, Pt-Co | 13 g[i] | | 4 G | 2 G | 80 | 30 | 30 | 80 | 18 G | | |

[a]MSO = mesityl oxide
[b]3,5,5-Trimethyl-3-Cyclohexene-1-one
[c]2,2,6-Trimethyl-5-cyclohexane-1,4-dione
[d]3,3,6,8-Tetramethyl-1-tetralone
[e]Non-volatile residues
[f]Grams of crude isophorone employed in the distillation
[g]Grams of each cut obtained. Total grams obtained = 294.4. The difference, 300 − 294.4 = 5.6 g, is hold-up in the distillation column.
[h]Not analyzed
[i]G = gardner color scale. All other data measured on the Pt-Co scale.
[j]Sodium level in the crude isophorone sample.
[k]Atomic adsorption
[l]Correcting for the amount of isophorone isomerized to TMCH (5.96 − 0.81) = 5.15 gives a recovery of 89.9% (246.66 + 5.15 = 251.81/280.20 × 100 = 89.9%).

Although the invention has been described in its preferred forms with a certain amount of particularity, it will be understood by those skilled in the art that the present disclosure has been made only by way of Example and that numerous changes can be made without departing from the spirit and scope of the invention.

I claim:

1. Method of refining crude isophorone made by the vapor phase reaction of acetone over a heterogeneous aldol condensation catalyst which comprises contacting said isophorone with aqueous caustic at a temperature of about 140° C. to about 200° C., washing the treated isophorone with water until the wash water has a pH of about 7 and recovering refined isophorone by a fractional distillation.

2. Method claimed in claim 1 wherein the causic is sodium hydroxide.

3. Method claimed in claim 2 wherein the concentration of sodium hydroxide is about 0.1 to about 0.8 weight percent based on the total charge.

4. Method claimed in claim 2 wherein the amount of sodium hydroxide used lies within the limits of about 0.01 to about 0.6 weight percent.

5. Method claimed in claim 1 wherein the caustic is lithium hydroxide.

6. Method claim in claim 1 wherein the caustic is potassium hydroxide.

7. Method claimed in claim 1 wherein the caustic is calcium oxide.

8. Method claimed in claim 1 wherein the caustic is magnesium hydroxide.

9. Method claimed in claim 1 wherein the temperature is about 140° C. to about 200° C.

* * * * *

UNITED STATES PATENT AND TRADEMARK OFFICE
CERTIFICATE OF CORRECTION

PATENT NO. : 4,434,301
DATED : February 28, 1984
INVENTOR(S) : Anthony Joseph Papa It is certified that error appears in the above—identified patent and that said Letters Patent is hereby corrected as shown below:

Column 4, line 1, after "lights" insert --fraction--.

Claim 2, line 1, delete "causic" and substitute therefor --caustic--.

Claim 7, line 1, after "claim" insert the numeral "1".

Signed and Sealed this

Nineteenth Day of June 1984

[SEAL]

Attest:

Attesting Officer

GERALD J. MOSSINGHOFF
Commissioner of Patents and Trademarks